United States Patent
Kawakami et al.

(10) Patent No.: US 11,179,346 B2
(45) Date of Patent: Nov. 23, 2021

(54) RUPATADINE-CONTAINING PATCH

(71) Applicants: TEIKOKU SEIYAKU CO., LTD., Kagawa (JP); J.URIACH Y COMPANIA S.A., Barcelona (ES)

(72) Inventors: Satoshi Kawakami, Sanuki (JP); Manabu Sogabe, Awa (JP)

(73) Assignees: TEIKOKU SEIYAKU CO., LTD., Kagawa (JP); J.URIACH Y COMPANIA S.A., Barcelona (ES)

( * ) Notice: Subject to any disclaimer, the term of this patent is extended or adjusted under 35 U.S.C. 154(b) by 0 days.

(21) Appl. No.: 16/605,237

(22) PCT Filed: Apr. 18, 2018

(86) PCT No.: PCT/JP2018/016692
§ 371 (c)(1),
(2) Date: Oct. 15, 2019

(87) PCT Pub. No.: WO2018/194183
PCT Pub. Date: Oct. 25, 2018

(65) Prior Publication Data
US 2020/0121612 A1 Apr. 23, 2020

(30) Foreign Application Priority Data
Apr. 19, 2017 (JP) .............................. JP2017-082559

(51) Int. Cl.
| A61K 9/70 | (2006.01) |
| A61K 31/4545 | (2006.01) |
| A61K 47/10 | (2017.01) |
| A61K 47/12 | (2006.01) |
| A61K 47/14 | (2017.01) |
| A61K 47/26 | (2006.01) |
| A61K 47/44 | (2017.01) |

(52) U.S. Cl.
CPC ........ *A61K 9/7061* (2013.01); *A61K 31/4545* (2013.01); *A61K 47/10* (2013.01); *A61K 47/12* (2013.01); *A61K 47/14* (2013.01); *A61K 47/26* (2013.01); *A61K 47/44* (2013.01)

(58) Field of Classification Search
CPC .... A61K 31/4545; A61K 47/10; A61K 47/12; A61K 47/14; A61K 47/26; A61K 47/44; A61K 9/7061; A61K 9/0014; A61K 31/445; A61K 31/55; A61K 47/38; A61K 9/0048; A61K 9/7053; A61K 9/7069; A61P 11/02; A61P 17/04; A61P 29/00; A61P 37/08; A61P 43/00; A61P 27/02; A61P 27/14
See application file for complete search history.

(56) References Cited

U.S. PATENT DOCUMENTS

| 5,407,941 | A | 4/1995 | Carceller et al. |
| 5,476,856 | A | 12/1995 | Carceller et al. |
| 2003/0035828 | A1* | 2/2003 | Tavares ................ A61P 37/08 424/449 |
| 2007/0166364 | A1 | 7/2007 | Beier et al. |
| 2009/0209632 | A1* | 8/2009 | Isowaki ............... A61K 9/0048 514/450 |

FOREIGN PATENT DOCUMENTS

| CN | 101933914 | 1/2011 |
| JP | 2730612 | 3/1998 |
| JP | 2009-500398 | 1/2009 |
| RU | 2 460 519 | 9/2012 |
| WO | 2009/001092 | 12/2008 |
| WO | 2012/001120 | 1/2012 |
| WO | 2013/158319 | 10/2013 |

OTHER PUBLICATIONS

Shamizadeh et al. "Rupatadine: efficacy and safety of a non-sedating antihistamine with PAF-antagonist effects", Allergo Journal International, 2014, vol. 23, No. 3, p. 87-95. (Year: 2014).*
International Search Report dated Jul. 3, 2018 in International (PCT) Patent Application No. PCT/JP2018/016692.
International Preliminary Report on Patentability dated Oct. 22, 2019 in International (PCT) Patent Application No. PCT/JP2018/016692.
Shamizadeh et al., "Rupatadine: efficacy and safety of a non-sedating antihistamine with PAF-antagonist effects", Allergo Journal International, 2014, vol. 23, No. 3, pp. 87-95.
Yanai et al., "The clinical pharmacology of non-sedating antihistamines", Pharmacology & Therapeutics, 2017, vol. 178, pp. 148-156.
Extended European Search Report dated Aug. 14, 2020 in corresponding European Patent Application No. 18788008.3.

* cited by examiner

*Primary Examiner* — Audrea B Coniglio
(74) *Attorney, Agent, or Firm* — Wenderoth, Lind & Ponack, L.L.P.

(57) ABSTRACT

An external patch that contains rupatadine as a second-generation antihistamine, has excellent plaster physical properties, good adhesion to applied skin, and good transdermal absorption of rupatadine as an active ingredient is provided. The external patch containing rupatadine uses an acrylic adhesive as an adhesive base. Specifically, the external patch containing rupatadine uses an acrylic adhesive as an adhesive base and further contains an organic acid having 2 to 7 carbon atoms as a solubilizer, a fatty acid ester as a softener, and/or a surfactant.

8 Claims, No Drawings

RUPATADINE-CONTAINING PATCH

TECHNICAL FIELD

The present invention relates to a rupatadine-containing external patch.

BACKGROUND ART

Rupatadine (general name), of which the chemical name is 8-chloro-11-[1-[(5-methyl-3-pyridinyl)methyl]-piperidin-4-ylidene]-6,11-dihydro-5H-benzo[5,6]cyclohepta[1,2-b]pyridine, is an N-alkylpyridine derivative having a platelet-activating factor (PAF) antagonism and an anti-histamine effect (Patent Document 1).

This compound has an anti-allergic effect and an anti-inflammatory effect. The efficacy thereof is improvement in allergic rhinitis including hay fever and pruritus associated with urticaria and skin diseases (eczema, dermatitis, and itchy skin). As a second-generation antihistamine, a tablet containing rupatadine fumarate, which is a pharmaceutically acceptable salt of rupatadine, as an active ingredient is approved and sold in 50 or more countries.

In Japan, the tablet containing rupatadine fumarate (rupatadine) has not been approved, and clinical development for approval has been investigated.

Since many of second-generation antihistamines used for therapy of allergic diseases have at least a sedative effect, there are problems in which adverse effects such as drowsiness occur during administration.

For this reason, a precaution of "alerting patients receiving the second-generation antihistamines to operations of machines involving risks, such as driving of automobiles" is imparted.

Rupatadine is classified as a second generation antihistamine, has less sedation, and side effects such as drowsiness are remarkably improved. However, when it is taken by oral administration, it is absorbed from the gastrointestinal mucosa and thereafter receives the first pass effect by the liver, so there is concern that the bioavailability will decrease. Regarding this point, when a patch is used, since the drug absorbed from the skin is circulated systemically by the blood flow, the first pass effect by the liver can be avoided and the bioavailability can be improved. Furthermore, in the case of a patch, it is possible to administer the drug stably over a long period of time as compared with oral administration. For these reasons, it is desired to develop a patch that can exhibit the medicinal effect of rupatadine with less absorption into the body and can stably administer the drug for a long period of time.

The provision of this external patch increases options of a drug (preparation) containing rupatadine, and is extremely useful from the viewpoint of patient compliance. However, formation of an external patch using rupatadine has not been investigated so far.

CITATION LIST

Patent Literature

Patent Literature 1: Japanese Patent No. 2730612

SUMMARY OF INVENTION

Technical Problem

An object of the present invention is to provide an external patch containing rupatadine, which has not been investigated so far.

Solution to Problem

In order to solve the problems, the present inventors have variously investigated. The inventors have investigated an adhesive base for development of a rupatadine-containing patch, and as a result, newly found that for the rupatadine-containing patch, an acrylic adhesive base is the most preferable among various adhesive bases. Thus, the present invention has been completed.

Specifically, a basic aspect of the present invention is:

(1) an external patch containing rupatadine characterized by using an acrylic adhesive as an adhesive base.

A specific aspect of the present invention is:

(2) the external patch according to the above-described (1) further containing any of a solubilizer, a softener, and a surfactant.

More specific aspects of the present invention are:

(3) the external patch according to the above-described (1) or (2), wherein rupatadine is contained in an amount of 3 to 20% by weight relative to a weight of a plaster;

(4) the external patch according to the above-described (2), wherein the solubilizer is added in an amount of 3 to 20% by weight relative to a weight of a plaster;

(5) the external patch according to the above-described (2), wherein the softener is added in an amount of 5 to 25% by weight relative to a weight of a plaster;

(6) the external patch according to the above-described (2), wherein the surfactant is added in an amount of 3 to 10% by weight relative to a weight of a plaster;

(7) the external patch according to the above-described (2), wherein an organic acid having 2 to 7 carbon atoms is added as the solubilizer;

(8) the external patch according to the above-described (7), wherein the organic acid is one selected from the group consisting of acetic acid, lactic acid, propionic acid, valeric acid, levulinic acid, and hexanoic acid;

(9) the external patch according to the above-described (2), wherein a fatty acid ester is added as the softener;

(10) the external patch according to the above-described (9), wherein the fatty acid ester is one or two or more kinds of fatty acid ester selected from the group consisting of oleyl oleate, isopropyl myristate, butyl stearate, isopropyl palmitate, dibutyl phthalate, diethyl phthalate, diisooctyl phthalate, diisobutyl phthalate, dicapryl phthalate, dinonyl phthalate, dimethylcyclohexyl phthalate, diethylhexyl phthalate, dibutyl sebacate, diethyl sebacate, diethylhexyl sebacate, dinonyl sebacate, diisooctyl sebacate, polypropylene sebacate, dimethoxy-cyclohexyl sebacate, dibutyl adipate, diethylhexyl adipate, dinonyl adipate, polypropylene adipate, dimethylcyclohexyl adipate, and dibutoxyethyl adipate; and

(11) the external patch according to the above-described (2), wherein one or a combination of two or more selected from the group consisting of a glycerol fatty acid ester, a sorbitan fatty acid ester, a polyoxyethylene fatty acid ester, a polyoxyethylene alkyl ether, and a polyoxyethylene hydrogenated castor oil is added as the surfactant.

The most preferable aspect of the present invention is:

(12) an external patch containing rupatadine characterized by using an acrylic adhesive as an adhesive base and further containing any of an organic acid having 2 to 7 carbon atoms as a solubilizer, a fatty acid ester as a softener, and a surfactant; and in particular,

(13) the external patch according to (12), wherein any of lactic acid and levulinic acid is added as the organic acid, and oleyl oleate and isopropyl myristate are added as the softener.

Advantageous Effects of Invention

The present invention provides an external patch that has good adhesion to applied skin due to excellent physical properties of a plaster, and good transdermal absorption of rupatadine as an active ingredient.

Under the current circumstances where an external patch containing rupatadine that is a transdermal absorption preparation has not been developed, the present invention particularly exhibits more excellent transdermal absorption due to use of an acrylic adhesive as an adhesive base than another adhesive base. Therefore, the present invention has a significant clinical effect.

DESCRIPTION OF EMBODIMENTS

As described above, the basic aspect of the present invention is an external patch containing rupatadine characterized by using an acrylic adhesive as an adhesive base.

Conventionally, rupatadine contained in the external patch of the present invention as an active ingredient is in a form of a free base of rupatadine, and a fumarate salt thereof is contained in such a tablet that has an oral administration dosage form. However, the external patch of the present invention preferably contains a free base of rupatadine.

The amount of rupatadine contained therein is not particularly limited as long as it is an amount sufficient to exert a desired beneficial effect by transdermal absorption. The contained amount thereof may be 3 to 20% by weight, and preferably 5 to 17% by weight relative to the weight of the plaster.

The present invention is an external patch in which rupatadine as such an active ingredient is contained in an adhesive base as a plaster ingredient. Results of investigation by the inventors have revealed that it is preferable that an acrylic adhesive be used as the adhesive base.

As an adhesive ingredient of the external patch, a rubber-based adhesive base such as a styrene-isoprene-styrene block copolymer (hereinafter abbreviated as SIS), isoprene, polyisobutylene (hereinafter abbreviated to PIB), a styrene-butadiene-styrene block copolymer (hereinafter abbreviated as SBS), and a styrene-butadiene rubber (hereinafter abbreviated as SBR), and a silicon-based adhesive base such as polyorganosiloxane are known. When the active ingredient of the present invention is rupatadine, it has been found that the acrylic adhesive is the most preferable in terms of skin permeability and adhesion.

Such an acrylic adhesive is not particularly limited as long as it is a copolymer containing at least one (meth)acrylic acid derivate represented by 2-ethylhexyl acrylate, methyl acrylate, butyl acrylate, hydroxyethyl acrylate, 2-ethylhexyl methacrylate, etc.

Specific examples thereof may include adhesives described in Iyakuhin Tenkabutu Jiten 2013 [Japanese Pharmaceutical Excipients Directory 2013] (edited by International Pharmaceutical Excipients Council Japan), such as an acrylic acid-acrylic acid octyl ester copolymer, a 2-ethylhexyl acrylate-vinyl pyrrolidone copolymer solution, an acrylic acid ester-vinyl acetate copolymer, a 2-ethylhexyl acrylate-2-ethylhexyl methacrylate-dodecyl methacrylate copolymer, an emulsion of methyl acrylate-2-ethylhexyl acrylate copolymer resin, and an acrylic polymer contained in an acrylic resin alkanolamine solution, and commercially available products, such as DURO-TAK acrylic adhesive series (available from Henkel), and EUDRAGIT series (available from Evonik Rohm Gmbh).

Furthermore, it has been found that in addition to the acrylic adhesive, the external patch of the present invention preferably further contain a solubilizer, a softener, and/or a surfactant.

The solubility of rupatadine in the acrylic adhesive is ensured at a certain level. However, the investigation by the inventors has revealed that it is better to make the solubility in the base more uniform using a dissolving agent to sufficiently ensure the skin permeability from the base.

Examples of such a solubilizer may include an organic acid having 2 to 7 carbon atoms, in particular. In a case of use of an organic acid having 8 or more carbon atoms, it is difficult to ensure sufficient solubility of rupatadine in the plaster ingredient. As a result, the skin permeability of rupatadine from the plaster may be reduced.

Examples of the organic acid having 2 to 7 carbon atoms may include acetic acid, lactic acid, propionic acid, valeric acid, levulinic acid (4-oxopentanoic acid), and hexanoic acid. In a case of levulinic acid and lactic acid (DL-lactic acid), good results were obtained.

The amount of such a solubilizer added is not limited as long as it is an amount sufficient to exert a desired beneficial effect by transdermal absorption. The amount thereof may be 3 to 20% by weight, and preferably 5 to 15% by weight relative to the weight of the plaster.

If the amount of the solubilizer added is less than 3% by weight, the solubility of the drug in a preparation may be reduced, and an undesired influence such as deposition of a crystal may occur. If it is more than 20% by weight, physical properties of the preparation may be affected.

In the external patch of the present invention, it is preferable that a softener be also added as a plaster ingredient. When a fatty acid ester among various softeners was used as such a softener, particularly good results were obtained.

Examples of such a softener may include fatty acid esters selected from the group consisting of oleyl oleate, isopropyl myristate, butyl stearate, isopropyl palmitate, dibutyl phthalate, diethyl phthalate, diisooctyl phthalate, diisobutyl phthalate, dicapryl phthalate, dinonyl phthalate, dimethylcyclohexyl phthalate, diethylhexyl phthalate, dibutyl sebacate, diethyl sebacate, diethylhexyl sebacate, dinonyl sebacate, diisooctyl sebacate, polypropylene sebacate, dimethoxy-cyclohexyl sebacate, dibutyl adipate, diethylhexyl adipate, dinonyl adipate, polypropylene adipate, dimethylcyclohexyl adipate, and dibutoxyethyl adipate. It is preferable that one kind of the fatty acid ester may be used or two or more kinds thereof may be used in combination.

In the external patch of the present invention, it is particularly preferable that a combination of oleyl oleate and isopropyl myristate be added. The amount of the combination added is not limited as long as it is an amount sufficient to exert a desired beneficial effect by transdermal absorption. The amount may be 5 to 25% by weight, and preferably 10 to 22% by weight relative to the weight of the plaster.

When the amount of the softener is less than 5% by weight, a desired permeability may not be obtained. When it is more than 25% by weight, the softener may be separated from the plaster to reduce physical properties of the plaster.

Further, it has been found that the external patch of the present invention preferably contains a surfactant as the plaster ingredient.

In the present invention, this surfactant is to be added in order to improve transdermal absorption since the surfactant is amphipathic. Specific examples thereof may include a glycerol fatty acid ester, a sorbitan fatty acid ester, a polyoxyethylene fatty acid ester, a polyoxyethylene alkyl ether, and a polyoxyethylene hydrogenated castor oil. One kind of the surfactant may be used or two or more kinds thereof may be used in combination.

The amount of the surfactant added is not limited as long as it is an amount sufficient to exert a desired beneficial effect by transdermal absorption. The amount thereof may be 3 to 10% by weight, and preferably 4 to 8% by weight relative to the weight of the plaster.

Further, various base ingredients used for a general external patch can be used for the external patch of the present invention as long as they do not affect the beneficial effects.

Such base ingredients are not particularly limited, and examples thereof may include water-soluble polymers such as polyvinylpyrrolidone, polyvinylalcohol, and polyacrylic acid; cellulose derivatives such as ethyl cellulose, hydroxypropyl cellulose, and hydroxypropyl methyl cellulose; silicon compounds such as silicic anhydride and light silicic anhydride; and inorganic fillers such as zinc oxide, aluminum oxide, titanium dioxide, silica, magnesium oxide, iron oxide, and stearic acid.

If necessary, a preservative, a refreshing agent, a sanitization agent, a flavoring agent, a coloring agent, or the like, can be added.

A support of the patch provided by the present invention is not particularly limited. As the support, an elastic or non-elastic support may be used.

Specifically, a film or sheet formed from a synthetic resin such as polyethylene terephthalate, polyethylene, polypropylene, polybutadiene, an ethylene-vinyl acetate copolymer, polyvinyl chloride, polyester, nylon, and polyurethane; a laminate, a porous film, a foam, a woven fabric, or a non-woven fabric thereof; or paper can be used.

For a release liner, polyethylene terephthalate, polypropylene, or paper can be used. In particular, polypropylene terephthalate (PET) is preferred.

The release liner may be subjected to a silicon treatment, if necessary, so that the release force is appropriate.

Hereinafter, one example of a method for producing the patch provided by the present invention and a patch preparation will be described.

Specifically, an organic acid having 2 to 7 carbon atoms as the solubilizer, a fatty acid ester as the softener, and the surfactant are weighed in a mixer, and an organic solvent having a boiling point of lower than 100° C., for example, ethyl acetate is added, to prepare an additive solution.

Subsequently, an acrylic adhesive and rupatadine are added to this additive solution, and the mixture is mixed with stirring until uniform to obtain a rupatadine-containing adhesive solution (plaster solution).

The resulting plaster solution is then spread on a release film (release liner) or a support, and dried for 4 to 20 minutes by a dryer of which the temperature in a drying furnace is adjusted to 60° C. or higher and lower than 80° C. After the organic solvent is removed by drying, the plaster layer is bonded to a support or a release film (release liner), to obtain the patch of the present invention.

The thickness of the plaster layer may be preferably 30 to 200 μm, particularly preferably 80 to 15 μm, and most preferably about 100 μm.

If the thickness of the plaster layer is less than 30 μm, the drug release is not sustained, and the adhesive force is reduced. If it is more than 200 μm, the amount of the drug contained in the plaster layer is increased, and the production cost is increased.

The resulting patch is finally cut into a desired size, and put into a packaging bag, to obtain a patch preparation of the present invention.

The aforementioned production method is a specific example of the production method, and is not limited. Various modification thereof can be made.

EXAMPLES

Hereinafter, the present invention will be described in detail by describing Examples, Comparative Examples, and Test Examples. However, the present invention is not particularly limited to these Examples.

Test Example 1: Investigation of Degree of Solubility of Rupatadine Free Base in Each Ingredient The degree of solubility of a rupatadine free base (sometimes also referred to as "rupatadine base") as an active ingredient in each plaster ingredient was investigated.

Levulinic acid as a solubilizer, oleyl oleate and isopropyl myristate (IPM) as a softener, and lauromacrogol (BL-4,2: polyoxyethylene lauryl ether) as a surfactant were selected. The degree of solubility of the rupatadine base in each ingredient was investigated.

For comparison, the degree of solubility of the rupatadine base in an acrylic adhesive as an adhesive base was also investigated.

<Test Method>

(1) HPLC Method

To 5 mL of each of levulinic acid, oleyl oleate, isopropyl myristate (IPM), and lauromacrogol (BL-4,2), an excessive amount of the rupatadine base was added and stirred. The mixture was filtered through a 0.45-μm membrane filter, to remove an undissolved substance. To 200 μL of the filtrate, methanol was added using a measuring flask to adjust the volume to a desired volume. The mixture was measured by HPLC.

A rupatadine concentration was measured by an external calibration curve method, and the degree of solubility was calculated by specific gravity conversion.

(2) Gravimetric Method

The degree of solubility of the rupatadine base in the acrylic adhesive was tested by a gravimetric method.

To 1 g (solid content) of the acrylic adhesive, the rupatadine base was added, and the mixture was stirred and degassed by ultrasonic wave.

The adhesive solution was applied so as to have a thickness of 100 μm, and dried. A plaster was observed by a microscope (manufactured by KEYENCE CORPORATION).

The degree of solubility was determined by the presence or absence of crystal.

<Results>

The degrees of solubility of rupatadine by the test methods are as described in Table 1 below.

TABLE 1

| Components | Purpose | Solubility (w/w %) |
|---|---|---|
| Levulinic acid | Solubilizer | 29 |
| Oleyl oleate | Softener | 2 |
| Isopropyl myristate | Softener | 2 |
| Lauromacrogol (BL-4,2) | Surfactant | 4 |
| Acrylic adhesive (OH group) *1 | Adhesive base | ≤15 to 16< |

*1: Acrylic pressure sensitive adhesive having OH group.

As seen from the results, the rupatadine base had a certain degree of solubility in the acrylic adhesive as an adhesive base, and by a combination with the solubilizer, more uniform solubility in the plaster was secured.

Test Example 2: In Vitro Hairless Rat Skin Permeability Test

A hairless rat skin permeability test was performed for an external patch of each of Examples and Comparative Examples by the following method.

<Test Method>

An excised abdominal skin of a male hairless rat (HWY series, 7 to 9 weeks old) was put in a Franz diffusion cell, and each test preparation (in Examples and Comparative Examples) cut into a round shape (φ 14 mm) was bonded to the skin. In a test, a receptor side was filled with phosphate buffered saline (PBS) containing 40% of polyethylene glycol 400, and hot water of 37° C. was circulated in a water jacket. A receptor liquid was sampled with time, and the content of rupatadine permeated through the skin was measured by liquid chromatography. A cumulative permeation amount after 24 hours from the start of the test was calculated.

<Results>

The results are described in each Table.

Test Example 3: Cohesive Force Test of Plaster

For the external patch in each of Examples and Comparative Examples, the cohesive force of a plaster was evaluated by the following method.

<Test Method>

One hour after production, an adhesive surface (plaster surface) of preparation of each external patch (in Examples and Comparative Examples) was pressed with a finger, and the finger was detached from the surface. Whether the adhesive layer (plaster) was attached to the skin (plaster remaining) was confirmed by visual observation.

The evaluation was made by "existence" or "non-existence."

<Results>

The results are described in each Table.

Examples 1 to 6: Investigation of Composition Ratio of Plaster Ingredient

A composition ratio of plaster ingredient in the external patch of the present invention was evaluated by a prescription described in Table 2 below.

TABLE 2

| Formulation | Examples | | | | | |
|---|---|---|---|---|---|---|
| | 1 | 2 | 3 | 4 | 5 | 6 |
| Levulinic acid | 14.00 | 10.00 | 10.00 | 12.50 | 10.00 | 5.00 |
| DL-Lactic acid | — | — | — | — | — | 5.00 |
| Oleyl oleate | 10.00 | — | 10.00 | 10.00 | 5.00 | 10.00 |
| Isopropyl myristate | — | 21.00 | 11.00 | 11.00 | 16.00 | 11.00 |
| Lauromacrogol (BL-4,2) | 5.00 | 5.00 | 5.00 | 5.00 | 5.00 | 5.00 |
| Acrylic adhesive (OH group) | 54.00 | 52.00 | 52.00 | 46.50 | 52.00 | 52.00 |
| Rupatadine Base | 17.00 | 12.00 | 12.00 | 15.00 | 12.00 | 12.00 |
| Organic acid/Rupatadine Base (molar ratio) | 2.95 | 2.99 | 2.99 | 2.99 | 2.99 | 3.42 |
| Cumulative Permeation Amount of Rupatadine (μg/cm$^2$) | 84.9 | 148.7 | 196.5 | 188.8 | 138.4 | 163.8 |
| Cohesive Force (Adhesive Deposit on the Finger) | Non | Non | Non | Non | Non | Small |

Examples 7 to 10: Investigation of Ratio of Solubilizer and Softener

An addition ratio of a solubilizer and a softener in the external patch of the present invention was evaluated and investigated by a prescription described in Table 3 below.

Levulinic acid as a solubilizer and oleyl oleate as a softener were selected. The ratio thereof was evaluated.

Further, these Examples were compared with Example 3 in which good results were obtained.

TABLE 3

| Formulation | Examples | | | | |
|---|---|---|---|---|---|
| | 7 | 8 | 9 | 10 | 3 |
| Levulinic acid | 15.00 | 12.50 | 7.50 | 5.00 | 10.00 |
| Oleyl oleate | 9.44 | 9.72 | 10.28 | 10.56 | 10.00 |
| Isopropyl myristate | 10.39 | 10.69 | 11.31 | 11.61 | 11.00 |
| Lauromacrogol (BL-4,2) | 4.72 | 4.86 | 5.14 | 5.28 | 5.00 |
| Acrylic adhesive (OH group) | 49.12 | 50.56 | 53.44 | 54.88 | 52.00 |
| Rupatadine Base | 11.33 | 11.67 | 12.33 | 12.67 | 12.00 |
| Organic acid/Rupatadine Base (molar ratio) | 4.74 | 3.84 | 2.12 | 1.41 | 2.99 |
| Cumulative Permeation Amount of Rupatadine (μg/cm$^2$) | 1.6 | 1.3 | 0.7 | 0.5 | 1.0 |
| Cohesive force (Adhesive Deposit on the Finger) | Non | Non | Small | Small | Non |

As seen from the results in Tables, even when oleyl oleate was used as a softener and the amount of levulinic acid added as a solubilizer was variously changed, good skin permeability of rupatadine as an active ingredient was obtained, and the physical properties of the plaster were excellent.

Examples 11 to 15: Investigation and Evaluation of Organic Acid as Solubilizer

The external patch of the present invention was investigated and evaluated depending on the kinds of organic acid having 2 to 7 carbon atoms as a solubilizer.

External patches of the present invention using organic acids described in Table 4 below as a solubilizer were evaluated.

TABLE 4

| Formulation | Examples | | | | |
|---|---|---|---|---|---|
| | 11 | 12 | 13 | 14 | 15 |
| Acetic acid (C2) | 5.50 | — | — | — | — |
| DL-Lactic acid (C3) | — | 7.60 | — | — | — |
| Propionic acid (C3) | — | — | 6.70 | — | — |
| Valeric acid (C5) | — | — | — | 9.00 | — |
| Hexanoic acid (C6) | — | — | — | — | 9.80 |
| Oleyl oleate | 10.50 | 10.27 | 10.37 | 10.11 | 10.02 |
| Isopropyl myristate | 11.55 | 11.29 | 11.40 | 11.12 | 11.02 |
| Lauromacrogol (BL-4,2) | 5.25 | 5.13 | 5.18 | 5.06 | 5.01 |
| Acrylic adhesive (OH group) | 54.60 | 53.39 | 53.91 | 52.58 | 52.12 |
| Rupatadine Base | 12.60 | 12.32 | 12.44 | 12.13 | 12.03 |
| Organic acid/Rupatadine Base (molar ratio) | 3.02 | 2.85 | 3.02 | 3.02 | 2.92 |
| Cumulative Permeation Amount of Rupatadine ($\mu g/cm^2$) | 64.2 | 140.3 | 42.6 | 79.5 | 59.2 |
| Cohesive force (Adhesive Deposit on the Finger) | Non | Non | Non | Non | Small |

Note:
numbers within brackets of organic acids are the number of carbons.

As seen from the results in Table, when an organic acid having 2 to 7 carbon atoms other than levulinic acid was used as a solubilizer and a fatty acid ester as a softener was added in combination, good skin permeability was obtained, and the physical properties of the plaster were excellent.

Example 16: Investigation of Acrylic Adhesive

An external patch of the present invention in which the kind of acrylic adhesive was changed was investigated and evaluated.

As an acrylic adhesive, an acrylic adhesive described in Table 5 below was used.
Acrylic adhesive (OH group): OH group-containing acrylic pressure-sensitive adhesive (Note: used in Example 3 described above)
Acrylic adhesive (having no functional group): acrylic pressure-sensitive adhesive having no functional group (non-functional)

TABLE 5

| Formulation | Examples | |
|---|---|---|
| | 16 | 3 |
| Levulinic acid | 10.00 | 10.00 |
| Oleyl oleate | 10.00 | 10.00 |
| Isopropyl myristate | 11.00 | 11.00 |
| Lauromacrogol (BL-4,2) | 5.00 | 5.00 |
| Acrylic adhesive (OH group) | — | 52.00 |
| Acrylic adhesive (Non-functional group) | 52.00 | — |
| Rupatadine Base | 12.00 | 12.00 |
| Organic acid/Rupatadine Base (molar ratio) | 2.99 | 2.99 |
| Cumulative Permeation Amount of Rupatadine ($\mu g/cm^2$) | 174.1 | 152.4 |
| Cohesive force (Adhesive Deposit on the Finger) | Non | Non |

As seen from the results described above, when the acrylic adhesive was used as an adhesive base, good skin permeability was obtained, and the physical properties of the plaster were excellent.

Comparative Examples 1 to 7: Investigation Depending on Kind of Adhesive

External patches in which an adhesive other than an acrylic adhesive was used as a plaster ingredient were evaluated.

The external patches of Comparative Examples 1 to 7 in accordance with a prescription in Table 6 were prepared and evaluated.

The patches of Comparative Examples 1 to 7 were prepared as follows.

A hydrogenated rosin glycerol ester was added to toluene and dissolved with stirring, a styrene-isoprene-styrene block copolymer (SIS) was added, and the mixture was stirred. After complete dissolution was confirmed, liquid paraffin was added to prepare an adhesive solution. To the resultant adhesive solution, an additive described in Table and rupatadine were added, and the mixture was mixed with stirring until uniform to obtain a rupatadine-containing adhesive solution. Subsequently, the rupatadine-containing adhesive solution was spread on a release liner of PET, and the solvent was removed by drying, to obtain an adhesive layer with a thickness of 100 μm. To the adhesive layer, a support of PET film was bonded, to obtain a patch of each of Comparative Examples.

TABLE 6

| Formulation | Comparative Examples | | | | | | |
|---|---|---|---|---|---|---|---|
| | 1 | 2 | 3 | 4 | 5 | 6 | 7 |
| Levulinic acid | — | — | 10.00 | 10.00 | 5.00 | 10.00 | 10.00 |
| Oleyl oleate | — | — | — | 3.00 | 8.00 | 15.00 | — |
| Lauromacrogol (BL-4,2) | — | — | — | — | — | — | 5.00 |
| SIS | 19.77 | 20.23 | 18.14 | 17.44 | 18.84 | 13.95 | 16.28 |
| Hydrogenated Rosin Glycerin Ester | 47.44 | — | 43.53 | 41.86 | 45.21 | 33.49 | 39.07 |
| Saturated Aliphatic Hydrocarbon Resin | — | 48.56 | — | — | — | — | — |
| Liquid paraffin | 17.79 | 18.21 | 16.33 | 15.70 | 16.95 | 12.56 | 14.65 |
| Rupatadine Base | 15.00 | 13.00 | 12.00 | 12.00 | 6.00 | 15.00 | 15.00 |
| Organic acid/Rupatadine Base (molar ratio) | | | 2.99 | 2.99 | 2.99 | 2.39 | 2.39 |
| Cumulative Permeation Amount of Rupatadine ($\mu g/cm^2$) | 22.6 | 10.1 | 15.3 | 11.9 | ND | ND | ND |

TABLE 6-continued

|  | Comparative Examples | | | | | | |
|---|---|---|---|---|---|---|---|
| Formulation | 1 | 2 | 3 | 4 | 5 | 6 | 7 |
| Cohesive force (Adhesive Deposit on the Finger) | Non | Non | Non | Small | Yes | Yes | Yes |

ND: Not tested.

From the results described above, when an adhesive base other than the acrylic adhesive was used as an adhesive base, the skin permeability of rupatadine as an active ingredient was considerably lower than that of the acrylic adhesive used in the present invention.

Comparative Examples 8 to 12: Investigation of Use of Organic Acid Other than Those Having 2 to 7 Carbon Atoms as Solubilizer External patches in which an organic acid (middle to long chain fatty acid: having 8 to 18 carbon atoms) other than the organic acid having 2 to 7 carbon atoms was used as a solubilizer were investigated and evaluated.

The external patches of Comparative Examples in accordance with a prescription in Table 7 were prepared and evaluated.

The external patches of Comparative Examples 8 to 12 were prepared as follows.

A middle to long chain fatty acid, a softener, and a surfactant described in Table were weighted, and ethyl acetate was added to prepare an additive solution.

To the resultant additive solution, an acrylic adhesive and rupatadine were added, and the mixture was mixed with stirring until uniform to obtain a rupatadine-containing adhesive solution. Subsequently, the rupatadine-containing adhesive solution was spread on a release liner of PET, and the solvent was removed by drying, to obtain an adhesive layer with a thickness of 100 μm. To the adhesive layer, a support of PET film was bonded, to obtain a patch of each of Comparative Examples.

TABLE 7

|  | Comparative Examples | | | | |
|---|---|---|---|---|---|
| Formulation | 8 | 9 | 10 | 11 | 12 |
| Caprylic acid (C8) | — | — | 12.25 | — | — |
| 2-Ethyl hexanoic acid (C8) | — | — | — | 12.25 | — |
| Nonanoic acid (C9) | — | — | — | — | 13.30 |
| Capric acid (C10) | 15.00 | — | — | — | — |
| Oleic acid (C18) | — | 24.50 | — | — | — |
| Oleyl oleate | 9.44 | 8.39 | 9.75 | 9.75 | 9.63 |
| Isopropyl myristate | 10.39 | 9.23 | 10.73 | 10.73 | 10.60 |
| Lauromacrogol (BL-4,2) | 4.72 | 4.19 | 4.87 | 4.87 | 4.82 |
| Acrylic adhesive (OH group) | 49.12 | 43.62 | 50.70 | 50.70 | 50.09 |
| Rupatadine Base | 11.33 | 10.07 | 11.70 | 11.70 | 11.56 |
| Organic acid/Rupatadine Base (molar ratio) | 3.20 | 3.58 | 3.02 | 3.02 | 3.02 |
| Cumulative Permeation Amount of Rupatadine (μg/cm$^2$) | 15.8 | 7.2 | 20.3 | 20.3 | 11.9 |
| Cohesive force (Adhesive Deposit on the Finger) | Non | Small | Non | Non | Small |

From the results in Table described above, in cases of use of an organic acid (middle to long chain fatty acid: having 8 to 18 carbon atoms) other than the organic acid having 2 to 7 carbon atoms, an external patch having excellent skin permeability was not obtained.

The results of Examples and Comparative Examples were evaluated together. As compared with the patches in Comparative Examples 1 to 7 using an adhesive other than an acrylic adhesive and the patches in Comparative Examples 8 to 12 using an organic acid having a larger number of carbon atoms as a solubilizer, the cumulative permeation amount in the external patches in Examples 1 to 16 of the present invention tended to be increased. This showed that specificity of the present invention could be well understood.

Among the patches in Examples 1 to 16 that each are the external patch of the present invention, in the respective patches in Examples 3 to 10, 12, and 16 using levulinic acid or DL-lactic acid as a solubilizer, oleyl oleate in combination with a fatty acid ester such as isopropyl myristate as a softener, and lauromacrogol as a surfactant, the cumulative permeation amount after 24 hours was very high.

INDUSTRIAL APPLICABILITY

As described above, the present invention provides an external patch containing rupatadine, which has not been investigated so far.

The external patch provided by the present invention contains rupatadine that is the second-generation antihistamine as an active ingredient. The external patch has excellent plaster physical properties and good transdermal absorption of rupatadine as an active ingredient. The external patch has great medical benefit.

The invention claimed is:

1. An external patch containing rupatadine, wherein an acrylic adhesive is used as an adhesive base and the external patch further comprises a solubilizer, a softener, and a surfactant, wherein
    the solubilizer is one or two or more kinds of organic acid having 2 to 7 carbon atoms selected from the group consisting of acetic acid, lactic acid, propionic acid, valeric acid, levulinic acid, and hexanoic acid;
    the softener is one or two or more kinds of fatty acid ester selected from the group consisting of oleyl oleate, isopropyl myristate, butyl stearate, isopropyl palmitate, dibutyl phthalate, diethyl phthalate, diisooctyl phthalate, diisobutyl phthalate, dicapryl phthalate, dinonyl phthalate, dimethylcyclohexyl phthalate, diethylhexyl phthalate, dibutyl sebacate, diethyl sebacate, diethylhexyl sebacate, dinonyl sebacate, diisooctyl sebacate, polypropylene sebacate, dimethoxy-cyclohexyl sebacate, dibutyl adipate, diethylhexyl adipate, dinonyl adipate, polypropylene adipate, dimethylcyclohexyl adipate, and dibutoxyethyl adipate; and
    the surfactant is one or a combination of two or more selected from the group consisting of a glycerol fatty acid ester, a sorbitan fatty acid ester, a polyoxyethylene fatty acid ester, a polyoxyethylene alkyl ether, and a polyoxyethylene hydrogenated castor oil.

2. The external patch according to claim 1, wherein rupatadine is contained in an amount of 3 to 20% by weight relative to a weight of a plaster.

3. The external patch according to claim 1, wherein the solubilizer is added in an amount of 3 to 20% by weight relative to a weight of a plaster.

4. The external patch according to claim 1, wherein the softener is added in an amount of 5 to 25% by weight relative to a weight of a plaster.

5. The external patch according to claim 1, wherein the surfactant is added in an amount of 3 to 10% by weight relative to a weight of a plaster.

6. The external patch according to claim 1, wherein the fatty acid ester is one or two or more kinds of fatty acid ester selected from the group consisting of oleyl oleate and isopropyl myristate.

7. The external patch according to claim 1, wherein a polyoxyethylene alkyl ether is added as the surfactant.

8. The external patch according to claim 1, wherein any of lactic acid and levulinic acid is added as the solubilizer, and oleyl oleate and isopropyl myristate are added as the softener.

* * * * *